United States Patent [19]

Tigliev

[11] Patent Number: 5,609,316

[45] Date of Patent: Mar. 11, 1997

[54] SUSPENSION SYSTEM FOR SURGICAL MICROSCOPE

[76] Inventor: George S. Tigliev, House 55, Apt. 190, 191104, St. Petersburg, Russian Federation

[21] Appl. No.: 523,765

[22] Filed: Sep. 5, 1995

[51] Int. Cl.$^6$ ............................................. F16M 11/00
[52] U.S. Cl. ........................... 248/123.11; 248/280.11; 248/281.11; 248/292.11; 248/586
[58] Field of Search ................ 248/123.11, 280.11, 248/281.11, 284.1, 292.11, 292.13, 276.1, 585, 586, 646, 665; 359/384

[56] References Cited

U.S. PATENT DOCUMENTS

| | | |
|---|---|---|
| 2,967,458 | 1/1961 | Stone . |
| 3,762,797 | 10/1973 | Heller . |
| 3,776,614 | 12/1973 | Kloots et al. . |
| 3,820,752 | 6/1974 | Oram ................................... 248/284.1 |
| 3,891,301 | 6/1975 | Heller . |
| 3,973,748 | 8/1976 | Nagasaka ............................... 248/586 |
| 4,076,351 | 2/1978 | Wyant ............................ 248/280.11 X |
| 4,332,426 | 6/1982 | Speicher . |
| 4,460,148 | 7/1984 | Sasaki .................................... 248/585 |
| 4,523,732 | 6/1985 | Biber et al. . |
| 4,548,373 | 10/1985 | Komura . |
| 4,640,062 | 2/1987 | Rubik ............................. 248/280.11 X |
| 4,741,607 | 6/1988 | Heller . |
| 4,815,832 | 3/1989 | Nagano et al. . |
| 4,881,709 | 11/1989 | Nakamura . |
| 4,953,822 | 9/1990 | Sharber et al. . |
| 5,074,651 | 12/1991 | Nagamine . |
| 5,288,043 | 2/1994 | Tigliev .............................. 248/123.11 |

FOREIGN PATENT DOCUMENTS 2804172  8/1979  Germany .......................... 248/280.11

*Primary Examiner*—Derek J. Berger

[57] ABSTRACT

A suspension system for a surgical instrument provides balancing in the vertical plane, and comprises a generally vertical support structure, a levered assembly extending out from the support structure, an attachment mechanism for mounting the surgical instrument to an outer member of the levered assembly, and a spring connected at a first end thereof to the levered assembly adjacent the attachment mechanism, movably extending across an upper portion of an inner member of the levered assembly, and connected at a second end thereof to a vertically movable portion of the levered assembly adjacent the support structure.

9 Claims, 2 Drawing Sheets

SUSPENSION SYSTEM FOR SURGICAL MICROSCOPE

BACKGROUND OF THE INVENTION

1. Field of the Invention.

The present invention relates to a suspension system for use with a surgical microscope and, more particularly, to such a suspension system with vertical movement balancing.

2. Description of Related Art.

In the field of medical technology there exists a need for a mobile surgical microscope suspension system that permits the rapid and nearly effortless movement of the microscope when desired. Illustrative prior suspension systems are disclosed in the following patents: U.S. Pat. No. 2,967,458; U.S. Pat. No. 3,762,797; U.S. Pat. No. 3,776,614; U.S. Pat. No. 3,891,301; U.S. Pat. No. 3,973,748; U.S. Pat No. 4,332,426; U.S. Pat No. 4,523,732; U.S. Pat No. 4,548,373; U.S. Pat. No. 4,741,607; U.S. Pat. No. 4,815,832; U.S. Pat. No. 4,881,709; U.S. Pat. No. 4,953,822; U.S. Pat. No. 5,074,651; and U.S. Pat. No. 5,288,043 (which has common inventorship hereto).

One special need that arises is to be able to move the surgical microscope in the vertical plane, ie. up and down, with a minimum of effort and with a relatively constant resistance or "drag". With all of the prior systems disclosed herein above, very accurate placement of the microscope is hampered by the draw backs inherent therein. Specifically, in prior suspension systems "vertical balancing" has been a problem. Vertical balancing is a desired ability to have the microscope move vertically with little or no inertial movement and with a consistency of smoothness of motion. To achieve vertical balancing, some prior systems use counterweights, such as in the "Contraves" suspension system marketed by Carl Zeiss A.G. of Germany. In other prior systems springs are used which work under compression, such as in the suspension systems used with the surgical microscopes marketed by Moeller.

With the counterweight systems, weights up to about 170–200 kg are used which cause very discernable residual or inertial moment which impairs the surgeon's ability to accurately and quickly position the microscope. With the springs systems, there is variable drag or resistance caused by the spring strength varying with its length of extension. As with the counterbalance systems, this variable spring drag does not permit the smooth and accurate placement of the surgical microscope at the desired height.

There exists a need for a suspension system that is used with surgical instruments that does not have the aforementioned problems.

SUMMARY OF THE INVENTION

The present invention has been contemplated to overcome the foregoing deficiencies and meet the above described needs. Specifically, the present invention is a suspension system for a surgical instrument that comprises a generally vertical support structure; a levered assembly extending out from the support structure; an attachment mechanism for mounting the surgical instrument to an outer member of the levered assembly; and spring means connected at a first end thereof to the levered assembly adjacent the attachment mechanism, movably extending across an upper portion of an inner member of the levered assembly, and connected at a second end thereof to a vertically movable portion of the levered assembly adjacent the support structure.

The present invention provides a balanced system that permits a surgical instrument to be moved smoothly and with a minimum of inertia movement by the fact that one end of the spring working in distraction is vertically movable and provides a constant strength of support to the surgical instrument while it is moved in the vertical plane.

DETAILED DESCRIPTION OF THE PREFERRED EMBODIMENTS

The present invention is a balanced suspension system for a surgical investigative instrument, which for the purposes of this discussion will be assumed to be a surgical microscope. However, it should be understood that any other type of instrument can be used with the present invention, such as eye and dental examination instruments. The term "balanced" is used to denote a system wherein the forces acting upon the instrument are canceled out so that the instrument can be moved with no or a minimum of inertia or residual force that tends to cause the instrument to drift, and so that a constant force is needed to move the instrument throughout its range of movement.

Figure 1:
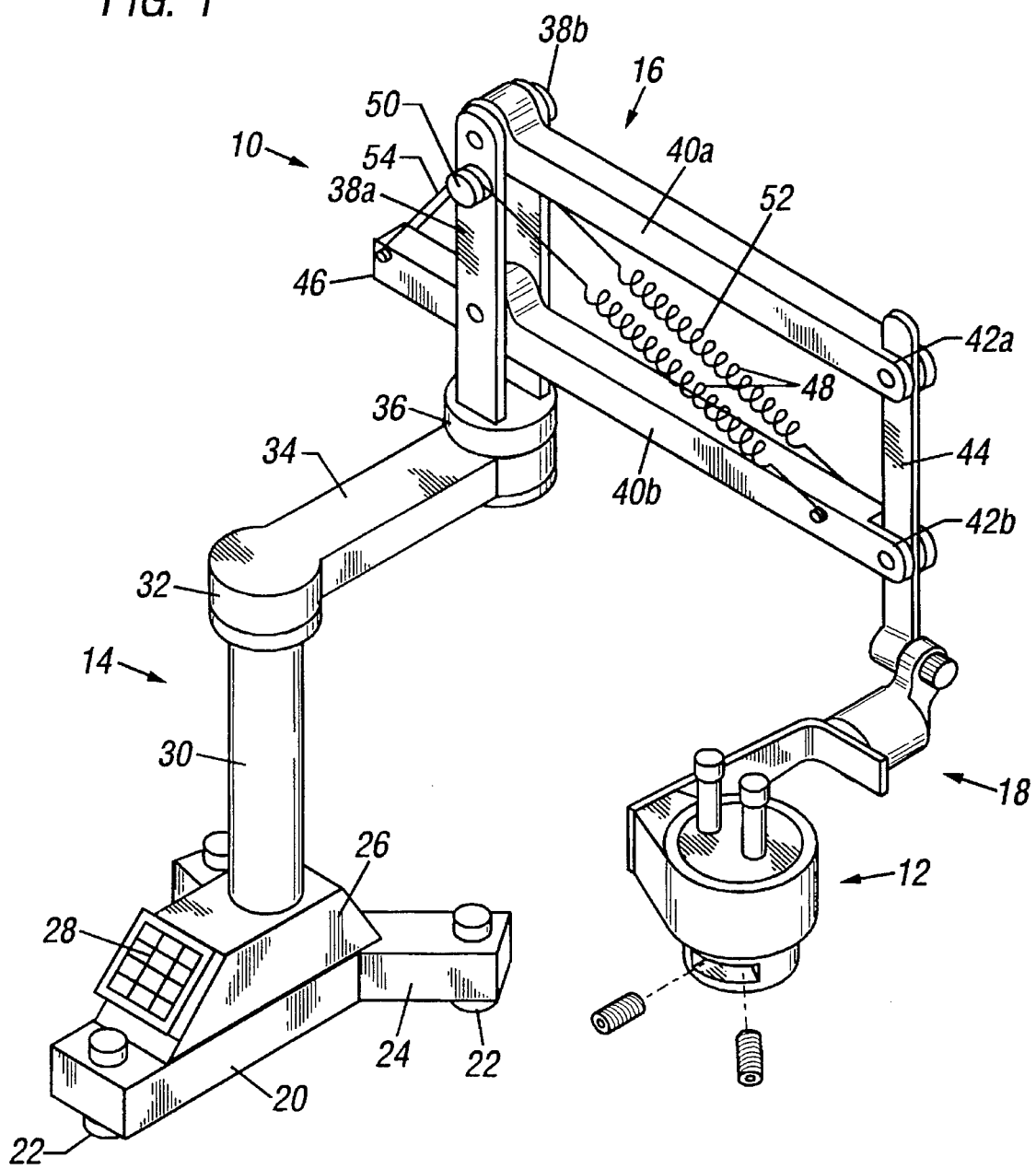
FIG. 1 is an upright, perspective view of a suspension system for use with a surgical instrument in accordance with one preferred embodiment of the present invention.

One preferred embodiment of the suspension system of the present invention is shown in FIG. 1 wherein a balance suspension system 10 for a surgical investigative instrument, such as a microscope 12, includes a generally vertical support structure 14, a levered assembly 16 extending from the support structure 14, and a mount assembly 18 extending from the levered assembly 16. The mount assembly 18 can be of any desired mount for connecting the microscope 12 to the suspension system 10, and most preferably is a balanced gimbal assembly shown in U.S. Pat. No. 5,288,043, which has common inventorship herewith.

The support structure 14 can be of any desired configuration that can provide stability and the desired range of movement. One preferred configuration includes a base 20, having adjustable elastomeric pads, wheels or rollers 22 on an underside thereof (if desired), and being of sufficient weight and having sufficient floor contacting surface area to provide the desired stability. The base 20 preferably includes outwardly extending legs 24. An electrical power supply 26 (interconnected to a source of AC or DC electrical power) and a control panel 28 are mounted to the base 20 and are in turn operatively electrically connected to the microscope 12.

Extending generally vertically from the base 20 is at least one support column 30 with a swivel joint member 32 attached to an upper end thereof, which permits radial rotation of a suspension arm 34 connected thereto in a horizontal plane about a vertical axis. At an opposite end of the suspension arm 34 is a swivel joint member 36, preferably of the same configuration as the joint member 32. The levered assembly 16, in the form of a pantograph, is connected to the suspension arm 34 at the joint member 36, so that the levered assembly 16 can be independently moved radially in a horizontal plane about a vertical axis. The microscope 12 in its mount assembly 18 is connected to an outer lower portion of the levered assembly 16, as will be described below.

The levered assembly 16 includes parallel support uprights 38a and 38b, which are inner members that can be attached to an upper portion of the column 30 or to the swivel joint member 32, as shown in FIG. 1, or they can be integrally formed as part of the column 30. Movably connected at one end to and lying between the support uprights 38a and 38b are spaced and parallel elongated members or pantograph arms 40a and 40b, each of which includes a yoke 42a and 42b respectively at an opposite end thereof. Movably connected to the yokes 42a and 42b is an outer member or secondary support upright 44, which is configured to move vertically and in a parallel manner with respect to the support uprights 38a and 38b. An extension member 46 extends outwardly through the support uprights 38a and 38b from an inner end of the pantograph arm 40b, so that as the secondary support upright 44 is moved vertically, an outer end of the extension member 46 is likewise moved vertically about a pivot point between the support uprights 38a and 38b.

One or more spring members 48 are attached at a first end therof to an outer end of the pantograph arm 40b, and at a second end thereof to an outer portion of the extension member 46. The spring members 48 movably extend across rotatable members 50, such as pulley wheels, that are mounted to an upper portion of the levered assembly 16, such as at or adjacent an upper end of the support uprights 38a and 38b. Preferably, the spring members 48 comprise a metallic heleical spring section 52 connected at a first end thereof to the outer portion of the pantograph arm 40b and connected at a second end thereof to a first end of a cable section 54. The cable section 54 comprises wire, cable or a Hall chain, and extends across the pulley wheels 50 at the upper portion of the support uprights 38a and 38b, and a second end of the cable section 54 is connected to the vertically movable extension member 46.

Figure 2:
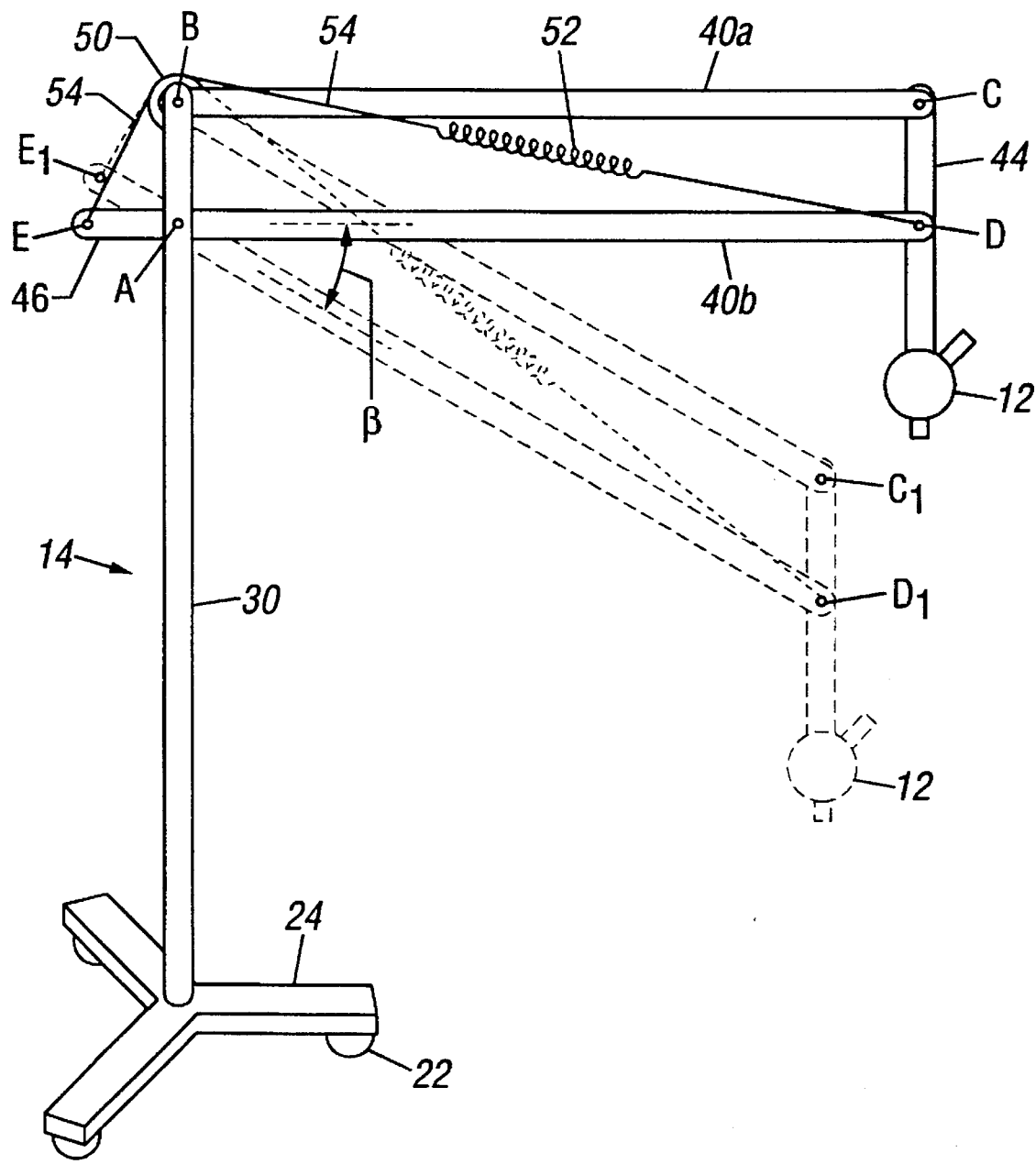
FIG. 2 is a semi-diagramatic elevational view of a suspension system for use with a surgical instruement in accordance with one preferred embodiment of the present invention.

The fact that the second end of the spring member 48 moves provides the desired vertical balancing as follows. For ease understanding reference will be made to the levered assembly 16 as a parallelogram ABCD, as shown in FIG. 2. The spring members 48 extend across the diagonal BD. The correlation of (a) the extension of the spring member 48, ie. the length of the diagonal BD, upon vertical movement of the arms of the parallelogram from position CD to C1D1 to (b) the length of the extension member 46 or AE are selected such that the movement of the point of fixation of the end of the spring member from E to E1 insures even support of the microscope 12 suspended from the secondary support upright 44, ie. the outer member CD, when moved through anble beta.

Whereas the present invention has been described in relation to the drawings attached hereto, it should be understood that other and further modifications, apart from those shown or suggested herein, may be made within the scope and spirit of the present invention.

What is claimed is:

1. A suspension system for a surgical instrument, comprising:

a generally vertical support structure;

a levered assembly extending out from the support structure;

attachment means for mounting the surgical instrument to an outer member of the levered assembly; and spring means connected at a first end thereof to the levered assembly adjacent the attachment means, movably extending across an upper portion of an inner member of the levered assembly, and connected at a second end thereof to a vertically movable portion of the levered assembly adjacent the support structure.

2. The suspension system of claim 1 wherein the levered assembly comprises a pantograph assembly having the outer member (CD) essentially parallel to the support structure, and pivotally connected to a first (BC) and a second (AD) essentially parallel elongated members.

3. The suspension system of claim 2 wherein the inner member (AB) is connected to the support structure, is essentially parallel to the outer member, and the first (BC) and the second (AD) elongated members are pivotally connected thereto.

4. The suspension system of claim 2 wherein the inner member (AB) is integral with an upper portion of the support structure, and the first (BC) and the second (AD) elongated members are pivotally connected thereto.

5. The suspension system of claim 2 wherein the vertically movable portion of the levered assembly comprises an extension member (AE) that extends from the second (AD) elongated member outwardly from a pivotal connection (a) with the inner member (AB).

6. The suspension system of claim 5 wherein the second end of the spring means is connected to the extension member (AE).

7. The suspension system of claim 1 wherein the upper portion of the inner member (AB) includes a rotatable bearing surface over which the spring means movably extends.

8. The suspension system of claim 7 wherein the rotatable bearing surface comprises a pulley wheel.

9. The suspension system of claim 1 wherein the spring means comprises a metallic spring section connected at a first end thereof to the outer member and connected at a second end thereof to a first end of a cable section, and the cable section extends across the upper portion of the inner member, and a second end of the cable section is connected to a vertically movable portion of the levered assembly adjacent the support structure.

* * * * *